United States Patent [19]

Baillie et al.

[11] Patent Number: 4,733,557
[45] Date of Patent: Mar. 29, 1988

[54] METHOD AND SYSTEM FOR DETERMINING VAPOR PRESSURE OR COMPOSITION OF HYDROCARBON LIQUIDS

[75] Inventors: Lloyd A. Baillie; James L. Skinner, both of Plano, Tex.

[73] Assignee: Atlantic Richfield Company, Los Angeles, Calif.

[21] Appl. No.: 921,919

[22] Filed: Oct. 22, 1986

[51] Int. Cl.[4] .............................................. G01N 7/00
[52] U.S. Cl. .......................................... 73/64.2; 73/53
[58] Field of Search ................... 73/64.2, 19, 61 R, 53

[56] References Cited

U.S. PATENT DOCUMENTS

| | | | |
|---|---|---|---|
| 3,738,154 | 6/1973 | Henry | 73/19 |
| 4,301,678 | 11/1981 | Gokcen | 73/64.2 |
| 4,348,117 | 9/1982 | Michels | 73/64.2 |

OTHER PUBLICATIONS

Spauschus, Automatic Vapor Pressure Measurements at Moderately High Pressure, Review of Scientific Instruments, Jun. 1961.

Primary Examiner—Stewart J. Levy
Assistant Examiner—Hezron E. Williams
Attorney, Agent, or Firm—Michael E. Martin

[57] ABSTRACT

The bubble point pressure, vapor pressure and liquid composition of hydrocarbon liquid flow streams is determined by causing the liquid flow stream to flow through a system having a plurality of eductors at selected various total pressure differentials across the eductors and measuring the pressure at the minimum pressure point or suction port of the eductors to obtain a reading of the vapor pressure. The system may comprise an array of three or more eductors arranged in parallel having flow regulating valves for controlling the flow rate and pressure drop across the eductors, respectively. The system may also comprise one eductor connected to a plurality of flow lines, each having flow control and/or shutoff valves arranged to provide for selective control of the flow rate and the resultant total pressure drop. Comparative data may be obtained for determining the liquid composition at a particular temperature based on the vapor pressure characteristics of known ranges of liquid compositions expected from the fluid stream being measured.

11 Claims, 5 Drawing Figures

METHOD AND SYSTEM FOR DETERMINING VAPOR PRESSURE OR COMPOSITION OF HYDROCARBON LIQUIDS

BACKGROUND OF THE INVENTION

1. Field of the Invention

The present invention pertains to a method and system for measuring the vapor pressure of a liquid, in particular a mixture of hydrocarbon liquids, wherein the liquid is sampled by flowing it through an eductor and the total pressure at the vapor or suction port of the eductor is measured as a function of the pressure differential of the liquid across the eductor at a given temperature.

2. Background

Liquids flowing through pipelines and process equipment, for example, often require the determination of the vapor pressure of the liquid and/or the approximate composition of the liquid so that operating conditions and/or liquid compositions may be controlled to avoid collection of volatile vapors or other operating problems. For example, liquid hydrocarbons being pumped through transmission pipelines and process equipment must be controlled to avoid the collection or dissemination of volatile vapors. Many liquid hydrocarbon flowstreams contain various liquid compositions and the exact or even approximate composition of the hydrocarbon mixture is difficult to determine or monitor under actual pipeline or process equipment operating conditions.

In the transport of crude oil through transmission pipelines from a gathering point to a refining or transfer point, the working pressures must be controlled or the inclusion of components such as natural gas liquids in the crude oil must be controlled to avoid dangerously high levels of volatile vapors. For example, if crude oil containing natural gas liquids (NGL) is being pumped through a pipeline system, the pumping pressures must be controlled or the quantity of NGL in the crude oil must be controlled to avoid a pressure condition wherein the more volatile liquids evaporate and result in the leakage of vapors from pumping equipment seals and other likely points of dangerous vapor accumulations.

One way to determine the vapor pressure of a particular liquid composition is by flowing the composition through a nozzle or eductor to lower the total pressure in the fluid flow stream to the point which is limited by the vapor pressure of the liquid. This condition can be rather easily reached for a liquid composition which is "pure" or does not include any dissolved gases. However, in the aforementioned situation involving the pumping of crude oil and other hydrocarbon liquids, for example, certain volatile dissolved gases and a variety of hydrocarbon compositions of different vapor pressure characteristics may be present in the liquid flow stream and an accurate reading of the vapor pressure by merely flowing the liquid through an eductor at a particular total differential pressure may not provide the actual vapor pressure of the composition being measured.

Moreover, it is important to determine, for a given composition of liquid having a particular quantity of dissolved gas, the pressure at which such dissolved gas begins to come out of solution to avoid the collection or dissolution of various vapors or gases. In regard to the aforementioned situations, the present invention has been developed with a view to providing a method and system for determining the actual pressure at which dissolved gases in a particular liquid composition will come out of solution, for determining the actual vapor pressure of a particular liquid composition and for determining the general composition of a liquid, particularly mixtures of liquid hydrocarbons being transported through pipelines and process equipment.

SUMMARY OF THE INVENTION

The present invention provides an improved method for determining the vapor pressure of a liquid composition. In accordance with one aspect of the invention the vapor pressure of a liquid composition is determined by selectively measuring the total pressure at the so-called vapor suction port of an eductor for selected flow rates which produce corresponding total pressure differentials across the eductor so as to ascertain when the total pressure at the vapor suction port has reached a substantially constant value corresponding to the vapor pressure of the liquid composition. In accordance with another aspect of the invention, the vapor pressure of a multicomponent liquid is detemined from plural measurements using one or more eductors to provide data which can be used to determine true vapor pressure of the composition.

In accordance with still another aspect of the present invention, a method is provided for determining the vapor pressure of a composition of liquid hydrocarbons flowing through a transmission pipeline or process equipment wherein not only the vapor pressure of the liquid composition may be determined but the pressure at which dissolved gases begin to come out of solution with the liquid composition, sometimes referred to as the bubble point, may be determined and so that process steps or flow control may be implemented to minimize any unwanted accumulations of gases or vapors.

In accordance with yet another aspect of the present invention there is provided a method for determining the approximate liquid composition of a liquid flow stream such as a liquid flow stream of crude oil having natural gas liquids (NGL) mixed therein so that acceptable levels of NGL mixtures in the crude oil may be maintained and monitored.

In accordance with yet another aspect of the present invention, there is provided a system for measuring the bubble point and/or the vapor pressure of a particular composition of liquids wherein the liquid composition is conducted through an eductor at selected flow rates to produce selected total differential pressures across the eductor and wherein the total pressure at the eductor vapor suction port is measured for each particular differential pressure. In one embodiment of the system, fluid is conducted simultaneously through a plurality of eductors at different flow rates and/or different pressure differentials across the eductors so that a plurality of total pressures may be obtained for determining the bubble point and the vapor pressure of the liquid composition.

In accordance with another embodiment of the system, a single eductor is arranged in a unique circuit to receive the liquid flow stream at different flow rates so that a plurality of pressure differentials and total pressures at the vapor suction port may be measured to determine the approximate bubble point of the fluid flow stream and the vapor pressure of the liquid composition in the flow stream.

The abovenoted features of the present invention, together with other superior aspects and advantages thereof will be further appreciated by those skilled in the art upon reading the detailed description which follows in conjunction with the drawing.

DESCRIPTION OF PREFERRED EMBODIMENTS

In the description which follows, like parts are marked throughout the specification and drawing with the same reference numerals. Certain features of the invention may be shown in the drawing in somewhat schematic form in the interest of clarity and conciseness.

In certain process systems where it is necessary or desirable to control vapor pressure in a flowing stream, a continuous measurement of vapor pressure can be made by passing a slipstream sample of liquid through an eductor and measuring the pressure at the eductor suction port. The suction port pressure will be the liquid vapor pressure, with certain qualifications, that is (1) the eductor must be operating at conditions which would generate a perfect vacuum if no vapor were being carried out with the liquid stream, and (2) if some of the liquid is vaporizing while passing through the eductor, then the pressure measured will be the vapor pressure of a liquid whose composition has been altered by the removal of this amount of vapor. The change in liquid composition will not occur if the liquid is a single compound, but may be important if the liquid includes small quantities of very light components such as air dissolved in water or methane in crude oil. The same consideration applies to vapor pressure measurements made in closed systems, where the vapor pressure may be a function of the ratio of vapor volume to liquid volume.

If a compound is present in liquid at a concentration of C moles per molar volume of liquid, and if the ratio of liquid phase to vapor phase concentrations for this substance is R, then the partial pressure P of this substance will be C/R atmospheres. Concentrations expressed in moles/molar volume of liquid are related to mole fraction by the formula:

$$\text{Mole fraction} = \frac{CM}{22400\rho} \quad \text{(a)}$$

where M is the mean molecular weight of the liquid and $\rho$ is liquid density. If a unit volume of liquid with an initial concentration C is permitted to come to equilibrium with a vapor space and the ratio of vapor volume to liquid volume is $\theta$, then the concentration in the vapor space will be at pressure P, and the concentration in the liquid will be RP. Therefore, $$C = \theta P + RP, \quad \text{(b)}$$

and $$P = \frac{C}{\theta + R}$$

The above expression applies to the partial pressure of a single component. In a complex mixture, total vapor pressure (P) could be expressed as:

$$P = \frac{C_1}{\theta + R_1} + \frac{C_2}{\theta + R_2} + \frac{C_3}{\theta + R_3} + \cdots \quad \text{(c)}$$

An equation of the type shown above has more constants than can be readily determined from a few data points. However, exponential equations of the type $P = Ae^{-B\theta}$, where A and B are constants and e is the base of natural logarithms, have properties which are very similar to those of the more complex equation above, and can be evaluated from two or three data points.

Figure 1:
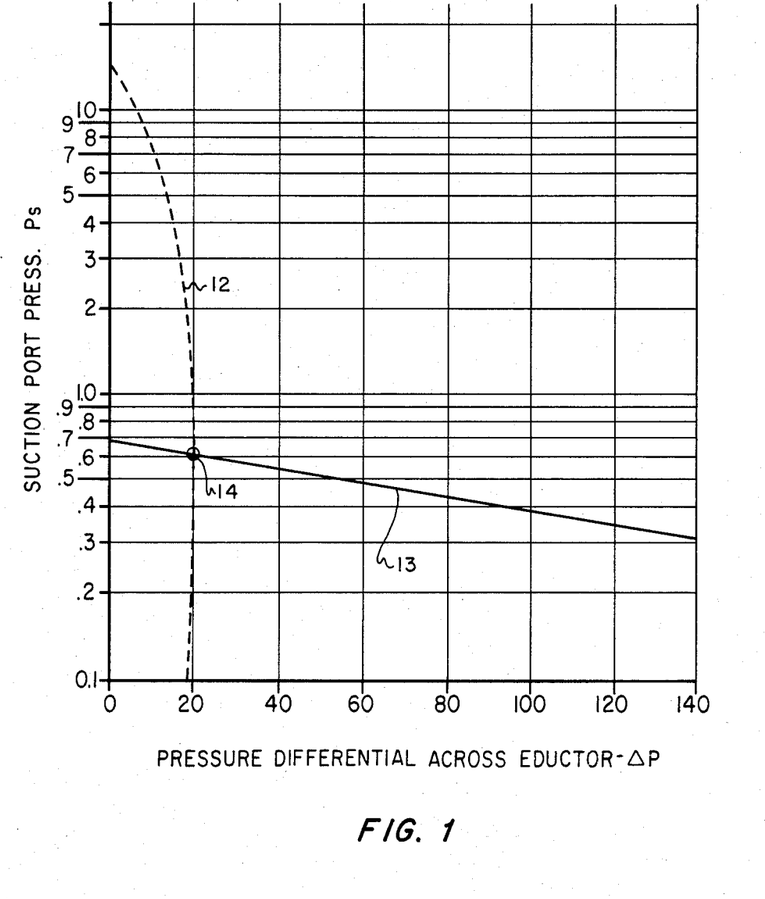
FIG. 1 is a diagram illustrating the pressure at the suction port of an eductor as a function of the differential pressure across the eductor.

When an eductor or jet pump is operated with liquid as the motive fluid and with no net inflow through the suction port, the suction port pressure is determined by one of two equations: on which applies to conditions where none of the pumping liquid is vaporized, and a second which applies to conditions where some of the pumping liquid is vaporized and carried out with the liquid. It has been determined that in a semilogarithmic graphical plot of eductor suction port pressure ($P_s$) versus the pressure differential across the eductor ($\Delta P$), see FIG. 1, the liquid-only curve 12 is approximately described by:

$$P_s = P_o - k_1 \Delta P^{k_2} \quad \text{(d)}$$

where $P_o$ is outlet pressure, $k_1$ is a constant having a value of 0.0108, and $k_2$ is a constant having a value of 2.40. When some of the pumping liquid is vaporizing, the eductor will find a pressure which will enable it to carry away all of the vapor which the liquid will produce at that pressure; that is, the vapor/liquid ratio of the liquid and that of the eductor must be the same at that pressure.

The vapor/liquid ratio of an eductor increases as pressure differential increases, although in a rather complex way. Nonetheless, it has been found that eductor suction pressure ($P_s$) varies with pressure differential across the eductor ($\Delta P$) according to an exponential equation analagous to the abovementioned equation relating vapor pressure (P) to $\theta$:

$$P_s = Ae^{-B\Delta P}$$

The constants A and B of this equation may be determined from a plot of suction port pressure versus differential pressure with as few as two data points taken at different pressure differentials. The curve 13 in FIG. 1, which describes partial vaporization conditions, will intersect the curve of the all-liquid condition described by the abovementioned equation (d). The point of intersection 14 of the curves 12 and 13 in FIG. 1 determines the highest pressure measured in psi (pounds per square inch) at which vaporization will occur, and is closely related to the bubble point, the true vapor pressure, and to the cavitation pressure.

In addition to the cavitation pressure, this analysis provides a second useful index of liquid quality. The slope B of the exponential curve will depend on the nature of the compounds causing the vapor pressure. In a liquid such as crude petroleum dissolved light gases such as methane, ethane, and $CO_2$ will result in a rapid change in vapor pressure with vapor volume (reflected in a high value of the slope B). On the other hand, vapor pressure resulting from the presence of heavier hydrocarbons will change little with vapor volume, resulting in a low value of B.

Figure 2:
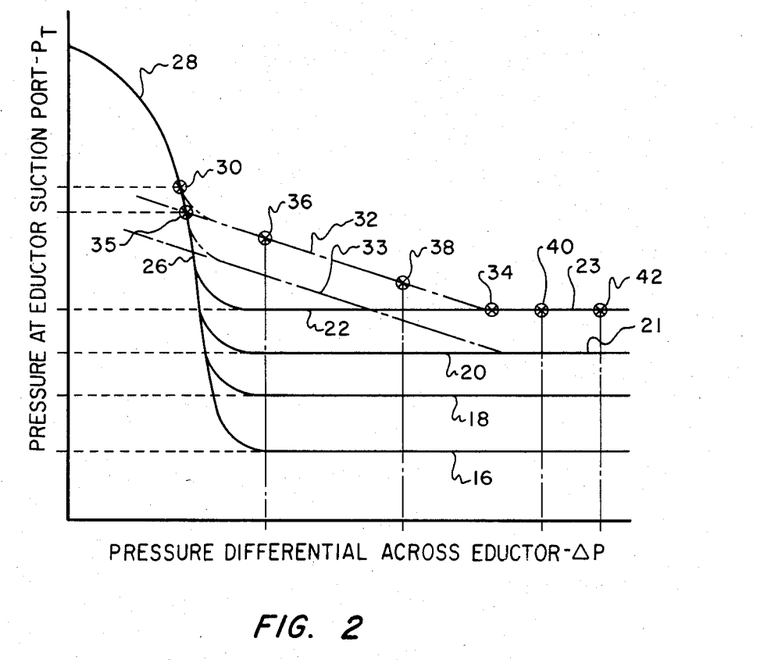
FIG. 2 is a diagram illustrating the total pressure at the vapor suction port of an eductor versus the pressure differential across the eductor for various liquid compositions and liquid compositions including dissolved gases.
Figure 3:
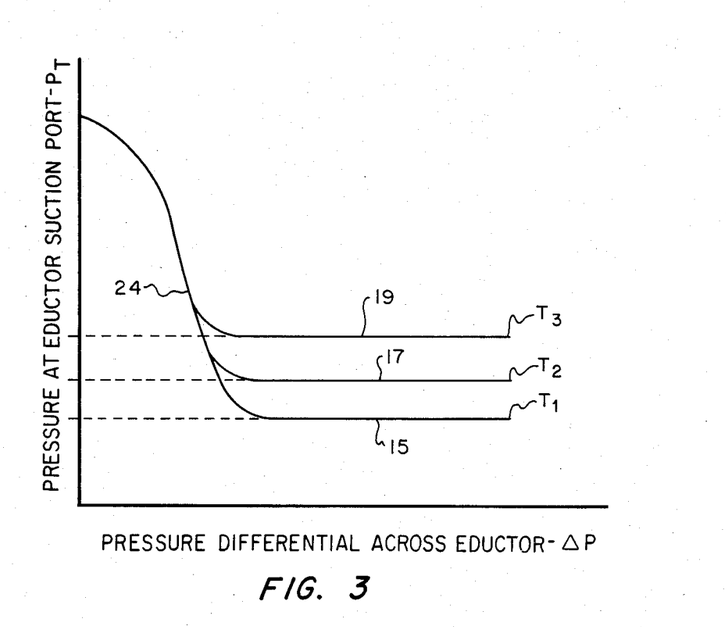
FIG. 3 is a diagram illustrating the pressure at the vapor suction port versus differential pressure across the eductor for a particular liquid composition at various liquid temperatures.

Referring now to FIGS. 2 and 3, these diagrams are similar to that of FIG. 1, and illustrate characteristics of liquids such as crude oil which comprise various compositions of hydrocarbons. Such compositions may be of relatively high molecular weight and are sometimes referred to as "dead" liquids in that they exhibit a very low vapor pressure characteristic. As indicated in FIG. 3, a liquid composition of relatively high molecular weight and of a certain substance, that is not a mixture of substances, and substantially free of dissolved gases exhibits a vapor pressure characteristic when conducted through an eductor such that, as the pressure differential across the eductor is increased, the pressure measured at the vapor suction port will decrease rather rapidly until reaching the vapor pressure of the liquid. In other words, the generally horizontal portions of curves 15, 17 and 19 indicate the vapor pressure of a particular liquid composition at selected temperatures $T_1$, $T_2$ and $T_3$, respectively, wherein $T_2$ is greater than $T_1$, and $T_3$ is greater than $T_2$. Accordingly, a known liquid composition will exhibit a particular vapor pressure at a particular temperature, although in light of the discussion hereinabove, the vapor pressure of a complex liquid will vary in such a way that the slope of the curves in FIGS. 2 and 3 are not truly zero. However, a heavy hydrocarbon liquid such as crude oil may have mixed therein various amounts of somewhat lower molecular weight hydrocarbon liquids such as natural gas liquids (NGL) which will cause the vapor pressure of the liquid mixture or composition to vary for a particular temperature.

FIG. 2 illustrates the approximate vapor pressure characteristic as determined by measuring the pressure at the suction port of an eductor versus the pressure differential across the eductor for various compositions of crude oil with natural gas liquids mixed therein at a given temperature. The curve 16 in FIG. 2, for example, may be considered as the characteristic of a particular crude oil having little or no low molecular weight hydrocarbon liquids mixed therewith whereas curves 18, 20, and 22, are the characteristics of crude oil mixed with varying quantities of natural gas liquids (NGL) wherein the composition of the liquid characterized by the curve 22 has a greater percent of NGL than the liquid characterized by the curve 20. The composition of the liquid characterized by the curve 20 has a greater percentage of NGL than the composition characterized by the curve 18. The characteristics of the liquids represented by the curves 16, 18, 20 and 22 are those which are measured at a constant temperature. It will be noted from FIGS. 2 and 3 that all of the curves 15, 17, 19, 16, 18, 20, and 22, have respective common portions indicated by the numerals 24 in FIG. 3 and 26, 28 in FIG. 2.

The points on these respective curves wherein the slope of the curve changes from the portion 24 or 26 to that represented by the remainder of the curves, with increasing pressure differential, is sometimes referred to as the bubble point or the point at which a relatively small bubble of vapor commences to form or bubbles of any dissolved gases in the liquid commence forming as the pressure of the liquid decreases. The determination of this actual bubble point pressure or a pressure slightly less can be of critical value in the handling of liquid compositions to prevent the dissolution of dissolved gases or the formation of vapors in various liquid treatment processes or, for example, in petroleum pipelining operations.

Although totally degassed or pure liquid compositions may be prepared after certain treatment processes, the gathering and transport of crude oils or mixtures of crude oils with other hydrocarbon liquids often result in certain amounts of entrained or dissolved gases being present in the liquid flow stream. Accordingly, the conduction of such a liquid flow stream with a particular amount of dissolved or entrained gas therein across an eductor will tend to develop a curve having the characteristics of, for example, a curve having a portion 28, as shown in FIG. 2, down to point 30 and a portion 32 extending from point 30 to point 34. When substances (for example, methane) having a significantly higher vapor pressure than that of the major components of the composition being measured have come out of solution the curve aligns with the generally horizontal extending curve 22 representing, for practical purposes, a substantially constant total pressure at the vapor suction port regardless of the pressure differential across the nozzle, in other words, the true vapor pressure of the liquid composition in question. Accordingly, a curve represented by the segments 23, 32, and 28 is a typical characteristic represented by a liquid such as crude oil having a certain amount of NGL mixed therein and also a certain amount of dissolved gases which are of substances having a substantially higher vapor pressure. The curve segment 32 is shown in somewhat simplified form as a substantially straight line although the segment may have a somewhat decreasing negative slope between the points 30 and 34. However, for purposes of one embodiment of a method and system of the present invention, it may be assumed that the plot of at least two operating conditions of the systems illustrated in FIGS. 4 and 5 may be used to develop the locus of an approximate bubble point for a particular liquid composition.

In accordance with the present invention, it is contemplated that laboratory testing of certain liquids or liquid mixtures may be carried out to develop a set of data representing the vapor pressure of crude oil substantially free of lower molecular weight hydrocarbons such as natural gas liquids and, for example, represented by the curve 16, 26, 28 in FIG. 2 while a crude oil having a first predetermined percentage of NGL would exhibit a characteristic exhibited by the curve 18, 26, 28 and crude oil compositions having higher concentrations of NGL's would be represented, respectively, by the curves 20, 26, 28 and 22, 23, 26, 28. In like manner, a liquid composition having a certain amount of dissolved gases therein might exhibit a characteristic corresponding to the curve 23, 32, 28. Of course, a crude oil having a certain NGL composition with some dissolved gases might also be represented by the curve 21, 33, 28. Data representing a particular crude oil with particular concentrations of NGL's at a given temperature could be stored in a suitable data source such as a microprocessor memory so that the measurement of flow conditions representing the points 36, 38, 40 and 42 may be utilized to determine the approximate bubble point of a liquid composition and the vapor pressure of the degassed liquid composition. This information is particularly useful for liquids being transported through pipeline systems and various types of processing equipment to prevent the formation of substantial quantities of vapor or to control such vapor formation within predetermined limits.

Figure 4:
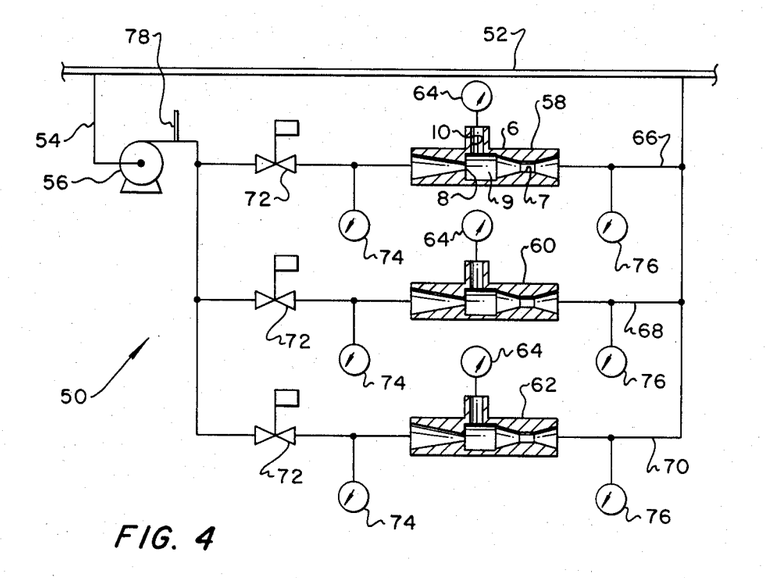
FIG. 4 is a schematic of one embodiment of a system for measuring vapor pressure of a liquid flow stream in accordance with the present invention.

One preferred system for carrying out a method of determining the approximate bubble point pressure and the vapor pressure at a particular temperature of a particular liquid composition is illustrated in FIG. 4. The system illustrated in FIG. 4 is generally designated by the numeral 50 and is particularly adapted for measuring the vapor pressure of and/or the composition of hydrocarbon liquid flowing through a transmission pipeline 52. The system 50 includes a conduit 54 which intersects the conduit 52 for removing a continuous sample of fluid therefrom and conduction to a pump 56 whereby the pressure of the liquid withdrawn from the pipeline may be raised to a suitable level to permit conduction of the liquid through respective eductors 58, 60 and 62.

In FIG. 4, eductor 58, by way of example, has a body 6 defining an outlet or throat 7 which is slightly larger in cross section than an orifice or nozzle 8 from which a jet of liquid is escaping. The space 9 between the orifice 8 and the outlet 7 is connected to a suction port 10, and is at a lower pressure when the eductor is operating than the eductor outlet 7. Each of the eductors 58, 60 and 62, is adapted to have sensing means such as a pressure gauge 64 arranged to measure the total pressure of the fluid at the suction port 10. The eductors 58, 60 and 62 are arranged in respective conduits 66, 68 and 70 which are suitably connected to the pump 56 and are also adapted to discharge liquid back into the transmission line 52.

Suitable flow control valves 72 are interposed in each of the conduits 66, 68 and 70 upstream of the respective eductors 58, 60 and 62 with respect to the direction of flow of liquid through the conduits. Suitable pressure measuring means such as gauges 74 and 76 are arranged to measure the pressure differential of fluid flowing through the respective eductors and suitable temperature measuring means 78 is provided for measuring the temperature of the liquid composition being discharged from the pump 56 to the respective conduits 66, 68 and 70. The aforementioned pressure and temperature sensing means may be adapted to provide suitable electrical signals which can be converted for digital computer processing to provide the desired vapor pressure readings using the equations mentioned herein.

For a system such as the system 50 to be used with crude oil transmission pipelines and the like, the conduits 66, 68 and 70 may be rather generously sized such as having nominal diameters ranging from one inch to two inches so that the eductors may also be of relatively large proportions to thereby minimize the chance of clogging the eductor nozzles with contaminants in the liquid being handled by the system. The mechanical simplicity of the system 50 is also advantageous for use in non-laboratory environments such as found in the oil and gas transport and processing industries.

In order to determine the vapor pressure of a liquid being pumped through the pipeline 52 on a continuous or intermittent basis, the pump 56 may be operated to withdraw a certain amount of fluid through the conduit 54 for discharge to the conduits 66, 68 and 70. The liquid flow rates through the respective conduits and the respective eductors 58, 60 and 62 may be adjusted so that different predetermined pressure differentials are measured across the eductors as well as the total pressure measured at the suction ports of the respective nozzles utilizing the pressure sensing means 64. The flow rate through at least one of the eductors 58, 60 and 62 may be determined to be sufficient to provide a substantial pressure drop across the eductor which will be in the region represented by and between the points 40 and 42 on the diagram of FIG. 2, for example. In this way, the vapor pressure of a particular liquid composition may be determined by taking a measurement of the total pressure at the suction port 10 for a differential pressure across the nozzle at a point such as the point 42 which is well beyond a range wherein the amount of dissolved gases expected to be present in the liquid composition would give a reading somewhere along the curve portion, for example. Accordingly, the eductors 58, 60 and 62 may be operated at respective flow rates of liquid therethrough which will simultaneously provide the data points 36 and 38 and at least one of the data points 34, 40 or 42.

Under testing conditions, the flow rate of liquid may be increased to give a pressure differential reading yet higher than that represented by the points 34, 40 or 42 to assure that the total pressure at the eductor suction port 10 remains substantially constant and therefore represents the vapor pressure of a degassed liquid composition. This vapor pressure may then be compared with the vapor pressures at the same temperature condition of known compositions of crude oil and natural gas liquid mixtures so that the actual composition of the liquid being measured can be determined. Moreover, establishment of the points 36 and 38 on the diagram of FIG. 2 will also provide for determining the slope of the curve portion 32 and the point of intersection, represented by the point 35 in FIG. 2, of the curve portion 32 with the curve portion 26. In this way, the approximate bubble point pressure of the liquid composition being measured can be determined and be conservatively estimated to be somewhat less than the true bubble point pressure represented by the point 30 in FIG. 2. Accordingly, for a liquid composition having a certain amount of dissolved gases which in themselves have vapor pressures higher than the vapor pressure of the liquid composition, the pressure at which these dissolved gases tend to come out of solution with the liquid mixture can be determined and operating conditions of a system handling the liquid composition in question may be maintained at a pressure greater than the approximate bubble point pressure to prevent or control degasification of the liquid.

Figure 5:
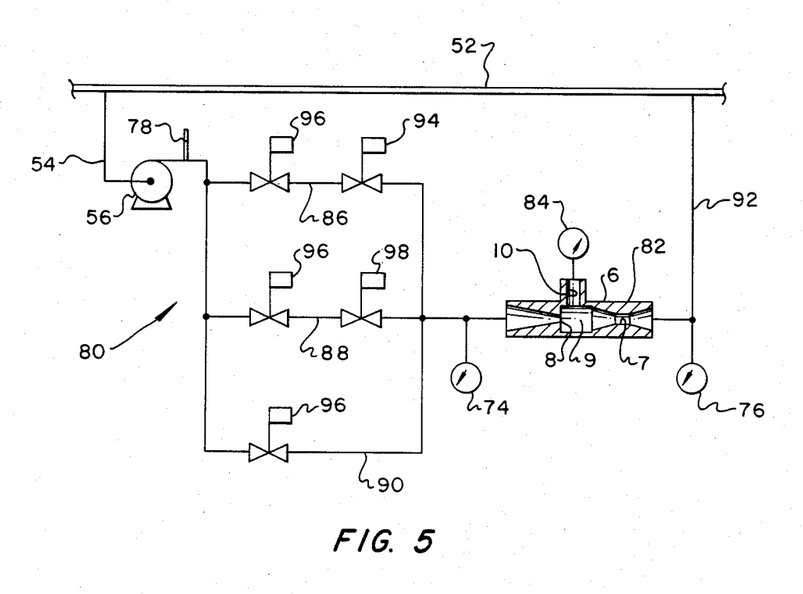
FIG. 5 is a schematic diagram of an alternate embodiment of a system in accordance with the present invention.

Referring now to FIG. 5, an alternate embodiment of a system for determining bubble point pressure, vapor pressure or composition of a particular liquid is illustrated and generally designated by the numeral 80. The system 80 is also adapted to be connected to a fluid transmission pipeline or the like such as the pipeline 52 and to receiving fluid therefrom on a continuous or intermittent basis through conduit 54 and pump 56. The system illustrated in FIG. 5 includes a single eductor 82 having the same features as the eductors 58, 60 and 62, including a suction port 10 at which pressure may be measured by pressure sensing means such as a gauge 84. Fluid is conducted from the pump 56 through the eductor 82 by way of one or more of conduits 86, 88 and 90 and returned to the pipeline by way of conduit 92. Pressure gauges 74 and 76 are interposed in the conduit on either side of the eductor 82 for measuring the total pressure differential across the eductor during various fluid flow conditions through the eductor. The conduit 86 has interposed therein a solenoid operated shutoff valve 94 and a flow control valve 96. The conduit 88 also has a flow control valve 96 and a solenoid operated valve 98 interposed therein and the conduit 90 has a flow control valve 96 interposed therein. Temperature of the fluid flowing through the system 80 may be measured by suitable temperature sensing means 78.

In the operation of the system 80, reading may be taken to establish the points 36, 38, 34, 40 and 42, for example, by selectively allowing flow through the conduits 86, 88 and 90. For example, a first reading may be taken by closing valves 94 and 98 and allowing flow through the eductor 82 by way of the conduit 90 only at a predetermined flow rate as set by valve 96 therein. An increased flow rate may be obtained by opening valve 94 whereupon a higher total differential pressure will be measured across the eductor. A still higher pressure differential across the eductor 82 may be obtained by opening both valves 94 and 98 so that flow is conducted through the eductor from all three of the conduits 86, 88 and 90. If fourth and fifth test points are required utilizing the system 80 the flow rate may be varied still further by adjusting one or more of the flow control valves 96, as required.

Accordingly, the systems illustrated in FIGS. 4 and 5 may be used to determine the bubble point pressure of a particular liquid composition having dissolved gas therein. These systems may be used to determine the vapor pressure of a particular liquid composition and, if vapor pressure data has been predetermined for a range of liquid compositions at various temperatures, the actual composition of the liquid being processed through the systems may also be determined from the vapor pressure measurements taken at the throat of the eductor or eductors used in the respective systems. Since the composition of a liquid being transported through a pipeline may be approximately known, the pressure differentials which are created across the eductors of the respective systems illustrated in FIGS. 4 and 5 may be set at relatively high pressures which will be higher than the pressure differential at which a liquid without any ingredients which would alter its composition or without any dissolved gas would exhibit its vapor pressure. Examples of eductor differential pressures at which crude oils having various quantities of NGL's mixed therein might be in the range of 30 psig, 50 psig, 120 psig, and 150 psig.

The methods and systems of the present invention advantageously enable the measurement of the intercept of the straight line portion or curve portion 32, for example, with the pressure variation curve for so-called "dead" crude oil so that the actual bubble point pressure represented by the point 35, for example, may be determined. This point is typically, for crude oils having various amounts of NGL blended thereinto, so close to the true bubble point pressure (often as small as 1.0 psi) that this difference can be experimentally determined for automatically estimating the true bubble point pressure of a particular liquid composition at a particular temperature when taking measurements using one or the other of the systems illustrated in FIGS. 1 and 2. Accordingly, various liquid hydrocarbon transport and storage systems can be protected against exceeding the allowable vapor pressure of the composition being handled by determining the intercept of the curve portion 32, for example, with the vapor pressure curve for "dead" crude oil. Moreover, if the approximate bubble point pressure, such as represented by the point 35 for the composition following the curve 28, 26, 32, 23 is used, a small margin of safety is built into the measurement since the approximate bubble point pressure is slightly less than the true bubble point pressure.

Moreover, if the bubble point pressure and the vapor pressure of a degassed liquid can be measured, such as represented by the points 35 and the points 34, 40 or 42, the amount of dissolved gas in the liquid composition in question may also be determined assuming that a predetermined correlation can be established with respect to the difference between the total pressure at the nozzle throat, the approximate bubble point pressure and the vapor pressure of the degassed liquid. This type of calculation can also be automatically determined by data processing equipment. Thus, by obtaining the total pressure at a nozzle throat at three points such as points 36, 38 and 40, the approximate bubble point pressure (or true bubble point pressure with correction), the vapor pressure, the composition of a particular liquid within a known range and the amount of dissolved gas in a liquid mixture can be determined. Although a preferred embodiment of the invention has been described in detail herein, those skilled in the art will recognize that various substitutions and modifications may be obtained without departing from the scope and spirit of the invention recited in the appended claims.

What is claimed is:

1. A method for determining the vapor pressure of a liquid composition of crude oil and natural gas liquids at a given temperature comprising the steps of:

causing the liquid composition to flow through eductor means while measuring the total pressure of the liquid at a location in said eductor means which comprises the minimum pressure point of fluid flow in said eductor means for a plurality of selected pressure differentials measured acorss said eductor means, said plurality of selected pressure differentials including at least one selected pressure differential which corresponds to a value which is known to provide the vapor pressure of said liquid composition;

determining the slope of a curve represented by the locus of the total pressure of the fluid at said minimum pressure point in said eductor means as a function of the selected pressure differential across said eductor means which produces said total pressure, respectively; and determining the intercept of said curve with a curve representing the relationship of total pressure at said minimum pressure point in said eductor means versus the pressure differential across said eductor means for a degassed liquid composition, which intercept comprises the bubble point pressure of said liquid composition.

2. The method set forth in claim 1 wherein:

said eductor means includes a plurality of separate eductors connected to conduit means for receiving a flow stream of said liquid composition; and said liquid composition is conducted through respective ones of said eductors at selected different total pressure differentials across said eductors, respectively and said total pressure at said minimum pressure point of each of said eductors is measured for said respective total pressure differentials across said eductors substantially simultaneously.

3. The method set forth in claim 1 wherein:

said eductor means is connected to conduit means for conducting a selected flow rate of said liquid composition through said eductor means to provide a plurality of pressure differentials across said eductor means corresponding to a plurality of total pressures measured at said minimum pressure point in said eductor means; and said liquid composition is caused to flow through said eductor means at selected flow rates as determined by causing said liquid to flow through one or more said conduit means.

4. A method for determining the composition of a mixture of crude oil and natural gas liquids at a given temperature comprising the steps of:

providing data comprising the vapor pressures of respective predetermined mixtures of crude oil and natural gas liquids at selected temperatures;

causing the liquid mixture in question to flow through eductor means while measuring the total pressure of said liquid mixture at a location in said eductor means which comprises the minimum pressure point of fluid flows in said eductor means for a plurality of selected pressure differentials measured across said eductor means;

determining when the slope of a curve represented by the locus of the total pressure at said minimum pressure point in said eductor means as a function of the selected pressure differential across said eductor means which produces said total pressure, respectively, is substantially zero; and comparing the total pressure value when said curve slope is substantially zero with said data representing the vapor pressures of said respective predetermined mixtures to determine the composition of the liquid being measured.

5. The method set forth in claim 4 including the step of:

determining the intercept of said curve with a curve representing the relationship of total pressure at said minimum pressure point in said eductor means versus the pressure differential across said eductor means for a degassed liquid composition, which intercept comprises the bubble point pressure of said liquid composition.

6. A method for determining the vapor pressure of a liquid composition such as crude oil and natural gas liquids at a given temperature comprising the steps of:

causing the liquid composition to flow through eductor means while measuring the total pressure at a fluid suction port in said eductor means for a plurality of selected pressure differentials measured across said eductor means;

determining the slope of a curve represented by the locus of the total pressure of the fluid at said suction port as a function of the selected pressure differential across said eductor means which produces said total pressure, respectively, by the equation:

$$P_s = A_e^{-B\Delta P}$$

wherein $P_s$ = total pressure at said suction port, A is a constant, B is the slope of said curve, e is the base of natural logarithms and $\Delta P$ is said selected pressure differential; and determining the intercept of said curve with a curve representing the relationship of total pressure at said suction port in said eductor means versus the pressure differential across said eductor means for a degassed liquid composition, which intercept is related to the bubble point pressure of said liquid composition.

7. A system for determining the vapor pressure of a liquid composition comprising crude oil and relatively low molecular weight hydrocarbon liquids comprising:

conduit means for withdrawing a sample of said liquid composition from a flowstream;

pump means connected to said conduit means;

a plurality of eductors connected to receive liquid from said pump means and having a construction whereby liquid flowing through said eductors reaches a minimum pressure at a predetermined point in said eductors, respectively;

said plurality of eductors being arranged in parallel for receiving liquid flowing from said pump means and including flow control means interposed between said eductors and said pump means for varying the flow rate of liquid through said eductors, respectively;

pressure sensing means for sensing the total pressure at said minimum pressure point in said eductors, respectively; and pressure sensing means for measuring the pressure differential across said eductors for liquid compositions flowing through said eductors, respectively.

8. The system set forth in claim 7 wherein:

said eductors each include a convergent nozzle and said pressure sensing means for measuring pressure at said minimum point includes pressure sensing means in communication with a suction port opening into said eductor for measuring the fluid pressure at said minimum pressure point.

9. The system set forth in claim 8 wherein:

a total of three eductors are provided in said system for making measurements of the pressures at said suction ports, respectively, for at least three different pressure differentials across said eductors.

10. A system for determining the vapor pressure of a liquid composition comprising crude oil and lower molecular weight hydrocarbon liquids comprising:

conduit means for conducting a sample of said liquid composition;

pump means connected to said conduit means;

eductor means connected for receiving liquid from said pump means and having a construction whereby liquid flowing through said eductor means reaches a minimum pressure at a predetermined point in said eductor means;

said conduit means comprising a plurality of conduits arranged in parallel for receiving liquid flowing from said pump means and including flow control regulating means interposed in said conduits between said eductor means and said pump means for varying the flow rate of liquid through said eductor means;

pressure sensing means for sensing the total pressure at said minimum pressure point in said eductor means, respectively; and pressure sensing means for measuring the pressure differential across said eductor means for respective flow rate of said liquid composition flowing through said eductor means, respectively.

11. The system set forth in claim 10 wherein:
said eductor means comprises a convergent nozzle and said pressure sensing means for measuring pressure at said minimum pressure point includes pressure sensing means in communication with a port opening into said eductor means for measuring the total fluid pressure at said minimum pressure point.

* * * * *